United States Patent
Yin et al.

(10) Patent No.: US 8,962,690 B2
(45) Date of Patent: Feb. 24, 2015

(54) COMPOSITIONS OF DIBROMOMALONAMIDE AND THEIR USE AS BIOCIDES

(75) Inventors: Bei Yin, Buffalo Grove, IL (US); Freddie L. Singleton, St. Charles, IL (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 13/388,070

(22) PCT Filed: Sep. 27, 2010

(86) PCT No.: PCT/US2010/050344
§ 371 (c)(1),
(2), (4) Date: Jan. 31, 2012

(87) PCT Pub. No.: WO2011/038318
PCT Pub. Date: Mar. 31, 2011

(65) Prior Publication Data
US 2012/0178817 A1 Jul. 12, 2012

Related U.S. Application Data

(60) Provisional application No. 61/246,187, filed on Sep. 28, 2009.

(51) Int. Cl.
*A01N 37/18* (2006.01)
*A01N 37/30* (2006.01)

(52) U.S. Cl.
CPC ..................................... *A01N 37/30* (2013.01)
USPC .......................................... 514/616; 424/405

(58) Field of Classification Search
CPC ....... A01N 37/30; A01N 25/30; A01N 33/12; A01N 47/44; A01N 2300/00
USPC .......................................... 514/616; 424/405
See application file for complete search history.

(56) References Cited

U.S. PATENT DOCUMENTS

| | | | |
|---|---|---|---|
| 4,163,795 A | | 8/1979 | Burk |
| 4,241,080 A | * | 12/1980 | Burk ............................. 514/528 |
| 4,661,503 A | * | 4/1987 | Martin et al. ................. 514/372 |
| 4,800,082 A | | 1/1989 | Karbowski et al. |
| 5,723,486 A | * | 3/1998 | Wu et al. ....................... 514/439 |
| 2003/0187073 A1 | | 10/2003 | Lichtenberg et al. |
| 2004/0261196 A1 | | 12/2004 | Ghosh et al. |
| 2005/0155937 A1 | * | 7/2005 | Zawada et al. ................ 210/758 |
| 2008/0142453 A1 | * | 6/2008 | Unhoch et al. ............... 210/755 |
| 2010/0096326 A1 | * | 4/2010 | Najmy et al. ................. 210/636 |

FOREIGN PATENT DOCUMENTS

| | | |
|---|---|---|
| JP | 6 256107 A | 9/1994 |
| JP | 2001213707 A | 8/2001 |
| WO | 2008076251 A2 | 6/2008 |
| WO | 2008091453 A1 | 7/2008 |

OTHER PUBLICATIONS

Toronto Research Chemicals Inc., "2,2-dibromomalonamide", 2004, by TRC catalog.*

* cited by examiner

*Primary Examiner* — Richard Schnizer
*Assistant Examiner* — Yanzhi Zhang
(74) *Attorney, Agent, or Firm* — Tifania M. Edwards

(57) ABSTRACT

A biocidal composition comprising 2,2-dibromomalonamide and a surface active biocide, and its use for the control of microorganisms in aqueous and water-containing systems.

6 Claims, No Drawings

COMPOSITIONS OF DIBROMOMALONAMIDE AND THEIR USE AS BIOCIDES

CROSS REFERENCE TO RELATED APPLICATIONS

This application is a 35 USC §371 national phase filing of PCT/US2010/050344 filed Sep. 27, 2010, which claims the benefit of U.S. Application No. 61/246,187, filed Sep. 28, 2009.

FIELD OF THE INVENTION

The invention relates to biocidal compositions and methods of their use for the control of microorganisms in aqueous and water-containing systems. The compositions comprise 2,2-dibromomalonamide and a surface active biocide.

BACKGROUND OF THE INVENTION

Water systems provide fertile breeding grounds for algae, bacteria, viruses, and fungi some of which can be pathogenic. Microbial contamination can create a variety of problems, including aesthetic unpleasantries such as slimy green water, serious health risks such as fungal, bacterial, or viral infections, and mechanical problems including plugging, corrosion of equipment, and reduction of heat transfer.

Biocides are commonly used to disinfect and control the growth of microorganisms in aqueous and water containing systems. However, not all biocides are effective against a wide range of microorganisms and/or temperatures, and some are incompatible with other chemical treatment additives. In addition, some biocides do not provide microbial control over long enough time periods.

While some of these shortcomings can be overcome through use of larger amounts of the biocide, this option creates its own problems, including increased cost, increased waste, and increased likelihood that the biocide will interfere with the desirable properties of the treated medium. In addition, even with use of larger amounts of the biocide, many commercial biocidal compounds cannot provide effective control due to weak activity against certain types of microorganisms or resistance of the microorganisms to those compounds.

It would be a significant advance in the art to provide biocide compositions for treatment of water systems that yield one or more of the following advantages: increased efficacy at lower concentrations, compatibility with physical conditions and other additives in the treated medium, effectiveness against a broad spectrum of microorganisms, and/or ability to provide both short term and long term control of microorganisms.

BRIEF SUMMARY OF THE INVENTION

In one aspect, the invention provides a biocidal composition. The composition is useful for controlling microorganisms in aqueous or water containing systems. The composition comprises: 2,2-dibromomalonamide and a surface active biocide selected from the group consisting of $C_{12}$-$C_{16}$ alkyl dimethyl benzyl ammonium chloride, dioctyl dimethyl ammonium chloride, polyhexamethylene biguanide, dodecylguanidine hydrochloride, and didecyldimethyl ammonium chloride.

In a second aspect, the invention provides a method for controlling microorganisms in aqueous or water containing systems. The method comprises treating the system with an effective amount of a biocidal composition as described herein.

DETAILED DESCRIPTION OF THE INVENTION

As noted above, the invention provides a biocidal composition and methods of using it in the control of microorganisms. The composition comprises: 2,2-dibromomalonamide and a surface active biocide selected from the group consisting of alkyl dimethyl benzyl ammonium chloride, dioctyl dimethyl ammonium chloride, polyhexamethylene biguanide, dodecylguanidine hydrochloride, and didecyldimethyl ammonium chloride. It has surprisingly been discovered that combinations of 2,2-dibromomalonamide and a surface active biocide as described herein, at certain weight ratios, are synergistic when used for microorganism control in aqueous or water containing media. That is, the combined materials result in improved biocidal properties than would otherwise be expected based on their individual performance. The synergy permits reduced amounts of the materials to be used to achieve the desired biocidal performance, thus reducing problems caused by growth of microorganisms in industrial process waters while potentially reducing environmental impact and materials cost.

For the purposes of this specification, the meaning of "microorganism" includes, but is not limited to, bacteria, fungi, algae, and viruses. The words "control" and "controlling" should be broadly construed to include within their meaning, and without being limited thereto, inhibiting the growth or propagation of microorganisms, killing microorganisms, disinfection, and/or preservation. In some preferred embodiments, "control" and "controlling" mean inhibiting the growth or propagation of microorganisms. In further embodiments, "control" and "controlling" mean the killing of microorganisms.

The term "2,2-dibromomalonamide" refers to a compound represented by the following chemical formula:

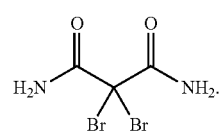

2,2-Dibromomalonamide and the surface active biocides of the invention are commercially available and/or can be readily prepared by those skilled in the art using well known techniques.

In some embodiments of the invention, the weight ratio of 2,2-dibromomalonamide to the surface active biocide is between about 100:1 and about 1:100.

In some embodiments, the weight ratio of 2,2-dibromomalonamide to the surface active biocide is between about 40:1 and about 1:20.

In some embodiments, the weight ratio of 2,2-dibromomalonamide to the surface active biocide is between about 32:1 and about 1:16.

In some embodiments, the surface active biocide is alkyl dimethyl benzyl ammonium chloride and the weight ratio of 2,2-dibromomalonamide to alkyl dimethyl benzyl ammonium chloride is from about 100:1 to about 1:20, alternatively from about 70:1 to about 1:10, alternatively from about 40:1 to about 1:1, alternatively from about 32:1 to about 2:1.

In some embodiments, the surface active biocide is dioctyl dimethyl ammonium chloride and the weight ratio of 2,2-dibromomalonamide to dioctyl dimethyl ammonium chloride is from about 100:1 to about 1:20, alternatively from about 70:1 to about 1:10, alternatively from about 20:1 to about 1:5, alternatively from about 9:1 to about 1:3, or alternatively from about 3:1 to about 1:3.

In some embodiments, the surface active biocide is polyhexamethylene biguanide and the weight ratio of 2,2-dibromomalonamide to polyhexamethylene biguanide is from about 100:1 to about 1:20, alternatively from about 70:1 to about 1:10, alternatively from about 10:1 to about 1:1, or alternatively from about 8:1 to about 2:1.

In some embodiments, the surface active biocide is dodecylguanidine hydrochloride and the weight ratio of 2,2-dibromomalonamide to dodecylguanidine hydrochloride is from about 100:1 to about 1:20, alternatively from about 20:1 to about 1:20, or alternatively from about 10:1 to about 1:16, alternatively from about 4:1 to about 1:16, or alternatively from about 1:1 to about 1:16.

In some embodiments, the surface active biocide is didecyldimethyl ammonium chloride and the weight ratio of 2,2-dibromomalonamide to didecyldimethyl ammonium chloride is from about 100:1 to about 1:20, alternatively from about 20:1 to about 1:20, or alternatively from about 10:1 to about 1:16, or alternatively from about 4:1 to about 1:16.

The composition of the invention is useful for controlling microorganisms in a variety of aqueous and water containing systems. Examples of such systems include, but are not limited to, paints and coatings, aqueous emulsions, latexes, adhesives, inks, pigment dispersions, household and industrial cleaners, detergents, dish detergents, mineral slurries polymer emulsions, caulks and adhesives, tape joint compounds, disinfectants, sanitizers, metalworking fluids, construction products, personal care products, textile fluids such as spin finishes, industrial process water (e.g. oilfield water, pulp and paper water, cooling water), oilfield functional fluids such as drilling muds and fracturing fluids, fuels, air washers, wastewater, ballast water, filtration systems, and swimming pool and spa water. Preferred aqueous systems are metal working fluids, personal care, household and industrial cleaners, industrial process water, and paints and coatings. Particularly preferred are industrial process water, paints and coatings, metal working fluids, and textile fluids such as spin finishes.

A person of ordinary skill in the art can readily determine, without undue experimentation, the effective amount of the composition that should be used in any particular application to provide microorganism control. By way of illustration, a suitable actives concentration (total for both 2,2-dibromomalonamide and surface active biocide) is typically at least about 1 ppm, alternatively at least about 3 ppm, alternatively at least about 7 ppm, alternatively at least about 10 ppm, or alternatively at least about 100 ppm based on the total weight of the aqueous or water containing system. In some embodiments, a suitable upper limit for the actives concentration is about 1000 ppm, alternatively about 500 ppm, alternatively about 100 ppm, alternatively about 50 ppm, alternatively about 30 ppm, alternatively about 15 ppm, alternatively about 10 ppm, or alternatively about 7 ppm, based on the total weight of the aqueous or water containing system.

The components of the composition can be added to the aqueous or water containing system separately, or preblended prior to addition. A person of ordinary skill in the art can easily determine the appropriate method of addition. The composition can be used in the system with other additives such as, but not limited to, surfactants, ionic/nonionic polymers and scale and corrosion inhibitors, oxygen scavengers, and/or additional biocides.

The following examples are illustrative of the invention but are not intended to limit its scope. Unless otherwise indicated, the ratios, percentages, parts, and the like used herein are by weight.

EXAMPLES

The results provided in the Examples are generated using a growth inhibition assay or a kill assay. Details of each assay are provided below.

Kill Assay.

This assay is used as a preliminary evaluation of synergy between the actives. The procedure is as follows. A mineral salts solution (0.2203 g of $CaCl_2$, 0.1847 g of $MgSO_4$, and 0.2033 g of $NaHCO_3$ in 1 L water, approximately pH 8) is inoculated with equal amounts (about $10^7 CFU/ml$) of a mixture of *Pseudomonas aeruginosa* ATCC 10145 and *Staphylococcus aureus* ATCC 6538. Aliquots of the cell suspension are then treated with 2,2-dibromomalonamide ("DBMAL"), a surface active biocide, and their combinations at various concentration levels. After incubating at 37° C. for 2 hours, the biocidal efficacy is determined on the basis of the minimum biocide concentration (MBC) needed to kill the bacterial cells in the aliquots. The MBC values are then used to calculate a synergy index (SI) values.

Summaries of the kill assay results are presented in the individual Examples. In each table, MBC values for each biocide and the blends tested are presented. Likewise, the Synergy Index ("SI") values for the combinations are listed. SI is calculated with the following equation:

$$\text{Synergy Index} = C_a/C_A + M_b/C_B$$

where $C_a$: Concentration of biocide A required for complete bacterial kill when used in combination with biocide B $C_A$: Concentration of biocide A required for complete bacterial kill when used alone $C_b$: Concentration of biocide B required for complete bacterial kill when used in combination with biocide A $C_B$: Concentration of biocide B required for complete bacterial kill when used alone The SI values are interpreted as follows:

SI<1: Synergistic

SI=1: Additive

SI>1: Antagonistic

Growth Inhibition Assay.

The growth inhibition assay used in the Examples measures inhibition of growth (or lack thereof) of a microbial consortium Inhibition of growth can be the result of killing of the cells (so no growth occurs), killing of a significant portion of the populations of cells so that regrowth requires a prolonged time, or inhibition of growth without killing (stasis). Regardless of the mechanism of action, the impact of a biocide (or combination of biocides) can be measured over time on the basis of an increase in the size of the community.

The assay measures the efficacy of one or more biocides at preventing growth of a consortium of bacteria in a dilute mineral salts medium. The medium contains (in mg/l) the following components: $FeCl_3.6H_2O$ (1); $CaCl_2.2H_2O$ (10); $MgSO_4.7H_2O$ (22.5); $(NH_4)_2SO_4$ (40); $KH_2PO_4$ (10); $K_2HPO_4$ (25.5); Yeast Extract (10); and glucose (100). After all components are added to deionized water, the pH of the medium is adjusted to 7.5. Following filter sterilization, aliquots are dispensed in 100 ul quantities to sterile microtiter plate wells. Dilutions of DBMAL and/or "Biocide B" are then added to the microtiter plate. After preparing the combinations of actives as illustrated below, each well is inoculated with 100 µl of a cell suspension containing ca. $1 \times 10^6$ cells per milliliter of a mixture of *Pseudomonas aeruginosa*, *Klebsiella pneumoniae*, *Staphylococcus aureus*, and *Bacillus subtilis*. The final total volume of medium in each well is 300 µl. Once prepared as described herein, the concentration of each active ranges from 25 ppm to 0.195 ppm as illustrated in Table 1. The resulting matrix allows testing of eight concentrations of each active and 64 combinations of actives in the ratios (of actives).

TABLE 1

Template for microtiter plate-based synergy assay showing concentrations of each active.

| | | Biocide B (mg/l) | | | | | | | |
|---|---|---|---|---|---|---|---|---|---|
| | | 25.0 | 12.5 | 6.25 | 3.125 | 1.563 | 0.781 | 0.391 | 0.195 |
| DBMAL | 25.0 | 1:1 | 1:2 | 1:4 | 1:8 | 1:16 | 1:32 | 1:64 | 1:128 |
| (mg/l) | 12.5 | 2:1 | 1 | 1:2 | 1:4 | 1:8 | 1:16 | 1:32 | 1:64 |
| | 6.25 | 4:1 | 2:1 | 1 | 1:2 | 1:4 | 1:8 | 1:16 | 1:32 |
| | 3.125 | 8:1 | 4:1 | 2:1 | 1 | 1:2 | 1:4 | 1:8 | 1:16 |
| | 1.563 | 16:1 | 8:1 | 4:1 | 2:1 | 1 | 1:2 | 1:4 | 1:8 |
| | 0.781 | 32:1 | 16:1 | 8:1 | 4:1 | 2:1 | 1 | 1:2 | 1:4 |
| | 0.391 | 64:1 | 32:1 | 16:1 | 8:1 | 4:1 | 2:1 | 1 | 1:2 |
| | 0.195 | 128:1 | 64:1 | 32:1 | 16:1 | 8:1 | 4:1 | 2:1 | 1:1 |

Ratios are based on weight (ppm) of each active.

Controls (not shown) contain the medium with no biocide added. After preparing the combinations of actives as illustrated above, each well is inoculated with 100 µl of a cell suspension containing ca. $1 \times 10^6$ cells per milliliter of a mixture of *Pseudomonas aeruginosa*, *Klebsiella pneumoniae*, *Staphylococcus aureus*, and *Bacillus subtilis*. The final total volume of medium in each well is 300 µl.

Immediately after the microtiter plates are prepared, the optical density (OD) readings for each well is measured at 580 nm and the plates are then incubated at 37° C. for 24 hr. After the incubation period, the plates are gently agitated before $OD_{580}$ values are collected. The $OD_{580}$ values at $T_0$ are subtracted from $T_{24}$ values to determine the total amount of growth (or lack thereof) that occurs. These values are used to calculate the percent inhibition of growth caused by the presence of each biocide and each of the 64 combinations. A 90% inhibition of growth is used as a threshold for calculating synergy index (SI) values with the following equation:

$$\text{Synergy Index} = M_{DBMAL}/C_{DBMAL} + M_B/C_B$$

where $C_{DBMAL}$: Concentration of DBMAL required to inhibit ~90% of bacterial growth when used alone $C_B$: Concentration of biocide (B) required to inhibit ~90% of bacterial growth when used alone.

$M_{DBMAL}$: Concentration of DBMAL required to inhibit ~90% of bacterial growth when used in combination with biocide (B).

$M_B$: Concentration of biocide (B) required to inhibit ~90% of bacterial growth when used in combination with DBMAL The SI values are interpreted as follows:

SI<1: Synergistic
SI=1: Additive
SI>1: Antagonistic

In the Examples below, the amounts of biocides in the solution are measured in mg per liter of solution (mg/l). Since solution densities are approximately 1.00, the mg/l measurement corresponds to weight ppm. Both units may therefore be used interchangeably in the Examples.

Example 1

DBMAL and DDAC

Kill Assay Results. Table 2 summarizes the results for assays using DBMAL alone and in combination with dioctyl dimethyl ammonium chloride ("DDAC"). As can be seen, several combinations demonstrate a synergistic effect.

TABLE 2

MBC (in mg/l) of DBMAL, DDAC, and combinations thereof

| Active weight ratio (1st:2nd) | 1st biocide DBMAL | 2nd biocide DDAC | Synergy Index |
|---|---|---|---|
| DBMAL alone | 66.7 | 0.0 | |
| 9:1 | 60.0 | 6.7 | <0.94 |
| 3:1 | 22.2 | 7.4 | <0.26 |
| 1:1 | 14.8 | 14.8 | <0.32 |
| 1:3 | 16.7 | 50.0 | <0.58 |
| 1:9 | 15.0 | 135.0 | <1.12 |
| DDAC alone | 0.0 | >150 | |

Example 2

DBMAL and ADBAC

Inhibition Growth Assay Results. Table 3 shows the inhibition growth assay results for DBMAL, $C_{12}$-$C_{16}$ alkyl dimethyl benzyl ammonium chloride ("ADBAC"), and combinations. The 90% inhibition of growth concentration ($I_{90}$) for DBMAL is 12.5 mg/l (Table 3). ADBAC is even more effective as only 3.13 mg/l is needed to meet the 90% inhibition of growth threshold. However, when combinations of these actives are tested, the results demonstrate lower concentrations of the two actives cause inhibition of growth. For example, 3.13 mg/l of DBMAL causes >90% inhibition of growth if as little as 1.56 mg/l of ADBAC is present.

TABLE 3

Percent inhibition of growth in a species-defined microbial consortium by ADBAC and DBMAL alone and combinations of these actives after a 24-hour incubation period.

| % Inhibition of growth in Untreated Control | Single Actives (mg/l) | | | | Combinations of DBMAL and ADBAC | | | | | | | | |
|---|---|---|---|---|---|---|---|---|---|---|---|---|---|
| | DBMAL Concn. (mg/l) | % Inhibition of growth by DBMAL | ADBAC Concn. (mg/l) | % Inhibition of growth by ADBAC | DBMAL Concn. (mg/l) | ADBAC Concn. (mg/l) | | | | | | | |
| | | | | | | 25.0 | 12.5 | 6.25 | 3.13 | 1.56 | 0.781 | 0.39 | 0.19 |
| 25 | 25.0 | 100 | 25.0 | 100 | 25.0 | 90 | 83 | 100 | 100 | 100 | 100 | 99 | 99 |
| 0 | 12.5 | 100 | 12.5 | 100 | 12.5 | 90 | 82 | 100 | 100 | 100 | 100 | 100 | 100 |
| 0 | 6.25 | 0 | 6.25 | 100 | 6.25 | 95 | 89 | 100 | 100 | 100 | 100 | 100 | 100 |
| 0 | 3.13 | 1 | 3.13 | 100 | 3.13 | 100 | 100 | 100 | 100 | 100 | 0 | 0 | 0 |
| 0 | 1.56 | 26 | 1.56 | 50 | 1.56 | 100 | 97 | 100 | 52 | 0 | 0 | 0 | 0 |
| 24 | 0.78 | 34 | 0.78 | 6 | 0.78 | 100 | 95 | 100 | 35 | 0 | 0 | 0 | 0 |
| 22 | 0.39 | 28 | 0.39 | 12 | 0.39 | 100 | 97 | 100 | 57 | 0 | 0 | 0 | 0 |
| 18 | 0.19 | 0 | 0.19 | 6 | 0.19 | 100 | 100 | 100 | 0 | 0 | 0 | 0 | 0 |

Numbers represent percent inhibition of growth as measured by optical density measurements (580 nm) at time = 24 hours compared with time = 0 values.

Table 4 shows ratios of DBMAL and ADBAC found to be synergistic under the growth inhibition assay.

TABLE 4

| DBMAL Concn. (mg/l) | ADBAC Concn. (mg/l) | Ratio (DBMAL to ADBAC) | Synergy Index (SI) |
|---|---|---|---|
| 6.25 | 0.78 | 8:1 | 0.75 |
| 6.25 | 0.39 | 16:1 | 0.63 |
| 6.25 | 0.19 | 32:1 | 0.56 |
| 3.13 | 1.56 | 2:1 | 0.75 |

Example 3

DBMAL and DGH

Inhibition Growth Assay Results. Table 5 shows the inhibition growth assay results for DBMAL, dodecylguanidine hydrochloride ("DGH"), and combinations thereof.

TABLE 5

Percent inhibition of growth in a species-defined microbial consortium by DGH and DBMAL alone and combinations of these actives after a 24-hour incubation period.

| % Inhibition of growth in Untreated Control | Single Actives (mg/l) | | | | Combinations of DBMAL and DGH | | | | | | | | |
|---|---|---|---|---|---|---|---|---|---|---|---|---|---|
| | DBMAL Concn. (mg/l) | % Inhibition of growth by DBMAL | DGH Concn. (mg/l) | % Inhibition of growth by DGH | DBMAL Concn. (mg/l) | DGH Concn. (mg/l) | | | | | | | |
| | | | | | | 25.0 | 12.5 | 6.25 | 3.13 | 1.56 | 0.78 | 0.39 | 0.19 |
| 0 | 25.0 | 100 | 25.0 | 100 | 25.0 | 100 | 100 | 96 | 98 | 98 | 100 | 100 | 100 |
| 1 | 12.5 | 98 | 12.5 | 100 | 12.5 | 100 | 100 | 97 | 100 | 100 | 100 | 99 | 52 |
| 0 | 6.25 | 5 | 6.25 | 52 | 6.25 | 100 | 100 | 100 | 99 | 100 | 0 | 0 | 0 |
| 5 | 3.13 | 1 | 3.13 | 3 | 3.13 | 100 | 100 | 99 | 99 | 0 | 0 | 0 | 0 |
| 0 | 1.56 | 0 | 1.56 | 0 | 1.56 | 100 | 100 | 99 | 37 | 0 | 0 | 0 | 0 |
| 0 | 0.78 | 3 | 0.78 | 0 | 0.78 | 100 | 100 | 97 | 0 | 0 | 0 | 0 | 0 |
| 10 | 0.39 | 3 | 0.39 | 3 | 0.39 | 100 | 100 | 72 | 0 | 0 | 0 | 0 | 0 |
| 10 | 0.19 | 11 | 0.19 | 5 | 0.19 | 100 | 100 | 85 | 0 | 0 | 0 | 0 | 0 |

Numbers represent percent inhibition of growth as measured by optical density measurements (580 nm) at time = 24 hours compared with time = 0 values.

Table 6 shows concentrations of DBMAL and DGH found to be synergistic. The ratios are based on concentrations (in mg/l) of the two actives.

TABLE 6

| DBMAL Concn. (mg/l) | DGH Concn. (mg/l) | Ratio (DBMAL:to DGH) | Synergy Index (SI) |
|---|---|---|---|
| 6.25 | 3.13 | 2:1 | 1.00 |
| 3.13 | 3.13 | 1:1 | 0.75 |
| 1.56 | 3.13 | 1:2 | 0.63 |
| 0.78 | 3.13 | 1:4 | 0.56 |
| 0.39 | 3.13 | 1:8 | 0.53 |
| 0.20 | 3.13 | 1:16 | 0.52 |
| 6.25 | 1.56 | 4:1 | 0.75 |
| 3.13 | 1.56 | 2:1 | 0.50 |

Example 5

DBMAL and DDMAC

Inhibition Growth Assay Results. Table 7 shows the inhibition growth assay results for DBMAL, didecyldimethyl ammonium chloride ("DDMAC"), and combinations thereof.

TABLE 8

| DBMAL Concn. (mg/l) | DDMAC Concn. (mg/l) | Ratio (DBMAL to DDMAC) | SI |
|---|---|---|---|
| 3.13 | 3.13 | 1:1 | 0.75 |
| 1.56 | 3.13 | 1:2 | 0.63 |
| 0.78 | 3.13 | 1:4 | 0.56 |
| 0.39 | 3.13 | 1:8 | 0.53 |
| 0.20 | 3.13 | 1:16 | 0.52 |
| 6.25 | 1.56 | 4:1 | 0.75 |
| 3.13 | 1.56 | 2:1 | 0.50 |

Example 6

DBMAL and PHMB

Inhibition Growth Assay Results. Table 9 shows the inhibition growth assay results for DBMAL, polyhexamethylene biguanide ("PHMB"), and combinations thereof.

TABLE 7

Percent inhibition of growth in a species-defined microbial consortium by DDMAC and DBMAL alone and combinations of these actives after a 24-hour incubation period.

| % Inhibition of growth in Untreated Control | Single Actives (mg/l) | | | | Combinations of DBMAL and DDMAC | | | | | | | | |
|---|---|---|---|---|---|---|---|---|---|---|---|---|---|
| | DBMAL Concn. (mg/l) | % Inhibition of growth by DBMAL | DDMAC Concn. (mg/l) | % Inhibition of growth by DDMAC | DBMAL Concn. (mg/l) | DDMAC Concn. (mg/l) | | | | | | | |
| | | | | | | 25.0 | 12.5 | 6.25 | 3.13 | 1.56 | 0.78 | 0.39 | 0.19 |
| 0 | 25.0 | 100 | 25.0 | 100 | 25.0 | 100 | 100 | 100 | 100 | 96 | 97 | 95 | 98 |
| 0 | 12.5 | 100 | 12.5 | 100 | 12.5 | 100 | 100 | 100 | 100 | 99 | 100 | 100 | 100 |
| 0 | 6.25 | 16 | 6.25 | 100 | 6.25 | 100 | 100 | 100 | 100 | 97 | 0 | 0 | 0 |
| 8 | 3.13 | 10 | 3.13 | 46 | 3.13 | 100 | 100 | 100 | 100 | 90 | 0 | 0 | 0 |
| 1 | 1.56 | 8 | 1.56 | 26 | 1.56 | 100 | 100 | 100 | 100 | 26 | 0 | 0 | 0 |
| 4 | 0.78 | 14 | 0.78 | 23 | 0.78 | 100 | 100 | 100 | 100 | 23 | 0 | 0 | 0 |
| 2 | 0.39 | 19 | 0.39 | 12 | 0.39 | 100 | 100 | 100 | 100 | 13 | 0 | 0 | 0 |
| 13 | 0.19 | 14 | 0.19 | 13 | 0.19 | 100 | 100 | 100 | 100 | 0 | 0 | 0 | 0 |

Numbers represent percent inhibition of growth as measured by optical density measurements (580 nm) at time = 24 hours compared with time = 0 values.

Table 8 shows concentrations of Concentrations of DBMAL and DDMAC found to be synergistic. The ratios are based on concentrations (in mg/l) of the two actives.

TABLE 9

Percent inhibition of growth in a species-defined microbial consortium by PHMB and DBMAL alone and combinations of these actives after a 24-hour incubation period.

| % Inhibition of growth in Untreated Control | Single Actives (mg/l) | | | | Combinations of DBMAL and PHMB | | | | | | | | |
|---|---|---|---|---|---|---|---|---|---|---|---|---|---|
| | DBMAL Concn. (mg/l) | % Inhibition of growth by DBMAL | PHMB Concn. (mg/l) | % Inhibition of growth by PHMB | DBMAL Concn. (mg/l) | PHMB Concn. (mg/l) | | | | | | | |
| | | | | | | 25.0 | 12.5 | 6.25 | 3.13 | 1.56 | 0.78 | 0.39 | 0.19 |
| 6 | 25.0 | 100 | 25.0 | 100 | 25.0 | 100 | 100 | 100 | 100 | 100 | 100 | 100 | 100 |
| 21 | 12.5 | 100 | 12.5 | 100 | 12.5 | 100 | 100 | 100 | 100 | 100 | 100 | 100 | 100 |
| 0 | 6.25 | 18 | 6.25 | 100 | 6.25 | 100 | 100 | 100 | 100 | 100 | 92 | 7 | 3 |
| 10 | 3.13 | 8 | 3.13 | 96 | 3.13 | 100 | 100 | 100 | 100 | 93 | 48 | 0 | 0 |
| 1 | 1.56 | 0 | 1.56 | 29 | 1.56 | 100 | 100 | 100 | 100 | 70 | 0 | 0 | 0 |
| 0 | 0.78 | 7 | 0.78 | 0 | 0.78 | 100 | 100 | 100 | 100 | 37 | 0 | 0 | 0 |
| 0 | 0.39 | 6 | 0.39 | 0 | 0.39 | 100 | 100 | 100 | 100 | 0 | 0 | 0 | 0 |
| 0 | 0.19 | 10 | 0.19 | 5 | 0.19 | 100 | 100 | 100 | 100 | 0 | 0 | 0 | 0 |

Numbers represent percent inhibition of growth as measured by optical density measurements (580 nm) at time = 24 hours compared with time = 0 values.

Table 10 shows concentrations of Concentrations of DBMAL and PHMB found to be synergistic. The ratios are based on concentrations (in mg/l) of the two actives.

TABLE 10

| DBMAL Concn. (mg/l) | PHMB Concn. (mg/l) | Ratio (DBMAL to PHMB) | Synergy Index (SI) |
|---|---|---|---|
| 6.25 | 0.78 | 8:1 | 0.75 |
| 3.13 | 1.56 | 2:1 | 0.75 |

While the invention has been described above according to its preferred embodiments, it can be modified within the spirit and scope of this disclosure. This application is therefore intended to cover any variations, uses, or adaptations of the invention using the general principles disclosed herein. Further, the application is intended to cover such departures from the present disclosure as come within the known or customary practice in the art to which this invention pertains and which fall within the limits of the following claims.

What is claimed is:

1. A synergistic biocidal composition for controlling microorganisms in an aqueous or water-containing system, the composition comprising: 2,2-dibromomalonamide and a surface active biocide selected from the group consisting of $C_{12}$-$C_{16}$ alkyl dimethyl benzyl ammonium chloride, dioctyl dimethyl ammonium chloride, polyhexamethylene biguanide, dodecylguanidine hydrochloride, and didecyldimethyl ammonium chloride:
   wherein when the surface active biocide is alkyl dimethyl benzyl ammonium chloride the weight ratio of 2,2-dibromomalonamide to alkyl dimethyl benzyl ammonium chloride is from 32:1 to 4:1
   wherein when the surface active biocide is dioctyl dimethyl ammonium chloride the weight ratio of 2,2-dibromomalonamide to dioctyl dimethyl ammonium chloride is from 9:1 to 1:3;
   wherein when the surface active biocide is polyhexamethylene biguanide the weight ratio of 2,2-dibromomalonamide to polyhexamethylene biguanide is from 32:1 to 2:1;
   wherein when the surface active biocide is dodecylguanidine hydrochloride the weight ratio of 2,2-dibromomalonamide to dodecylguanidine hydrochloride is from 1:1 to 1:16; and
   wherein when the surface active biocide is didecyldimethyl ammonium chloride the weight ratio of 2,2-dibromomalonamide to didecyldimethyl ammonium chloride is from 4:1 to 1:16.

2. The composition according to claim 1 which is: paint, coating, aqueous emulsion, latex, adhesive, ink, pigment dispersion, household or industrial cleaner, detergent, dish detergent, mineral slurry polymer emulsion, caulk, adhesive, tape joint compound, disinfectant, sanitizer, metalworking fluid, construction product, personal care product, textile fluid, spin finish, industrial process water, oilfield functional fluid, fuel, air washer, wastewater, ballast water, filtration systems, or swimming pool and spa water.

3. A method for controlling microorganism growth in an aqueous or water-containing system, the method comprising treating the aqueous or water-containing system with an effective amount of a composition according to claim 1.

4. The method according to claim 3 wherein the aqueous or water-containing system is paint, coating, aqueous emulsion, latex, adhesive, ink, pigment dispersion, household or industrial cleaner, detergent, dish detergent, mineral slurry polymer emulsion, caulk, adhesive, tape joint compound, disinfectant, sanitizer, metalworking fluid, construction product, personal care product, textile fluid, spin finish, industrial process water, oilfield functional fluid, fuel, air washer, wastewater, ballast water, filtration system, or swimming pool and spa water.

5. The method according to claim 3 wherein the composition inhibits the growth of microorganisms in the aqueous or water-containing system.

6. The method according to claim 3 wherein the composition kills microorganisms in the aqueous or water-containing system.

* * * * *